United States Patent
Li et al.

(10) Patent No.: US 11,155,812 B2
(45) Date of Patent: Oct. 26, 2021

(54) ONE-STEP SURFACE MODIFICATION TO GRAFT DNA CODES ON PAPER AND ITS BIO-APPLICATIONS

(71) Applicants: Xiujun Li, El Paso, TX (US); Wan Zhou, El Paso, TX (US)

(72) Inventors: Xiujun Li, El Paso, TX (US); Wan Zhou, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 735 days.

(21) Appl. No.: 15/826,072

(22) Filed: Nov. 29, 2017

(65) Prior Publication Data

US 2018/0155714 A1 Jun. 7, 2018

Related U.S. Application Data

(60) Provisional application No. 62/428,921, filed on Dec. 1, 2016.

(51) Int. Cl.
*C12Q 1/6837* (2018.01)
*C12N 15/10* (2006.01)

(52) U.S. Cl.
CPC ..... *C12N 15/1093* (2013.01); *C12N 15/1006* (2013.01); *C12Q 1/6837* (2013.01); *B01L 2300/0819* (2013.01)

(58) Field of Classification Search
CPC ........ B01L 2300/0819; C12N 15/1006; C12N 15/1093; C12Q 1/6837
See application file for complete search history.

(56) References Cited

U.S. PATENT DOCUMENTS

2012/0135437 A1* 5/2012 Brennan ............. G01N 33/552
435/18

OTHER PUBLICATIONS

Saal et al. (Mater. Res. Soc. Symp. Proc., 2005, 873E:K9.3.1-6) (Year: 2005).*
Araujo et al., *Anal. Chem.*, 2012; 84:3311-17.
Chao et al., *Biosens. Bioelectron*, 2016; 81:92-96.
Christ et al., *Chemistry*, 2011; 17:8524-28.
Demirel, *Chemphyschem.*, 2014; 15:1693-99.
Dou et al., *Anal Chem.*, 2014; 86:7978-86.
Dou et al., *Biosens. Bioelectron.*, 2016; 87:865-73.
Dou et al., *Taianta*, 2015; 145:43-54.
Fritz et al., *Proc. Natl. Acad. Sci. USA.*, 2002; 99:14142-46.
Guan et al., *Bioresources*, 2015; 10:1587-98.
He et al., *Anal. Chem.*, 2013; 85:1327-31.
James and Martin, *Biochem J.*, 1952; 50:679-90.
Kao and Hsu, *Microfluid Nanofluid*, 2014; 16:811-18.
Koga et al., *J. Mater. Chem.*, 2011; 21:9356-61.
Le Berre et al., *Nucleic Acids Res.*, 2003; 31:88-95.
Li et al., *J. Am. Chem. Soc.*, 2002; 124:9639-47.
Liu et al., *Lab Chip* 2011; 11:1041-48.
Malekghasemi et al., *Taianta*, 2016; 159:401-11.
Niu et al., *Chem. Commun.*, 2008; 4463-65.

(Continued)

*Primary Examiner* — Jeremy C Flinders
(74) *Attorney, Agent, or Firm* — Norton Rose Fulbright US LLP (57) ABSTRACT

Embodiments described herein are related to a one-step surface modification method with 3-aminopropyl trimethoxysilane (APTMS), which was developed and applied for DNA immobilization on a paper-based device via the ionic adsorption.

13 Claims, 8 Drawing Sheets

(56) References Cited

OTHER PUBLICATIONS

Park et al., *Bioconjug. Chem.*, 2010; 21:1246-53.
Pirrier et al., *Anal. Chem.*, 2004; 76: 1352-58.
Sanjay et al., *Analyst*, 2015; 140: 7062-81.
Sanjay et al., *Sci Rep-Uk*, 2016; 6:30474-83.
Schlapak et al., *Langmuir*, 2006; 22:277-85.
Shalev et al., *Sensors*(Basel), 2009; 9:4366-79.
Wang and Bard, *Anal. Chem.*, 2001; 73:2207-12.
Wang and Li, *J. Agric. Food Chem.*, 2007; 55:10509-16.
Yang et al., *Langmuir*, 2006; 22:11245-50.
Yu et al., *Langmuir*, 2012; 28:11265-73.
Zammatteo et al., *Analytical biochemistry*, 2000; 208: 143-50.
Zhang and Lee, *Appl. Surf. Sci.*, 2015; 327:233-40.
Zhao et al., *Biosens. Bioelectron.*, 2016; 79:581-88.

\* cited by examiner

ONE-STEP SURFACE MODIFICATION TO GRAFT DNA CODES ON PAPER AND ITS BIO-APPLICATIONS

BACKGROUND

DNA microarray is widely used for numerous applications. In past decades, the conventional substrate for DNA microarray is the glass slide (Zammatteo et al., *Analytical biochemistry* 2000, 280:143-50). A significant increase in the development of glass-based devices for biomolecule isolation, detection, and analysis has been achieved in microarray technology and point-of-care diagnostic testing. For instance, an aldehyde-functionalized glass slide was employed by Li et al. (*Sci Rep-Uk* 2016, 6:30474-83) to support the flexible DNA microarray construction for the successful detection of greenhouse plant fungal pathogens in minutes. Another efficient acid-mediated method was proposed by Park et al. (*Bioconjug. Chem.* 2010, 21:1246-53) as a part of the procedures for the construction of microarrays, obtaining the N-hydroxysuccinimide ester (NHS)-functionalized glass surface to study the biomolecular interactions, which was suitable for efficient immobilization of various probes appended by amine, hydrazide, and alcohol functionalities. Very recently, Wang et al. improved the glass surface modification and demonstrated a universal and highly sensitive DNA microarray for the detection of sequence-specific DNA via the dextran scaffold-functionalized instead of the aldehyde-functionalized glass surface (Chao et al., *Biosens. Bioelectron.* 2016, 81:92-96).

Despite these developments, as the traditional capable substrate used in the microarray technology for the DNA detection, there are still some unfavorable factors about glass slides, such as the complicated fabrication process, low probe density on the 2D glass surface, expensive modified glass sides, the need of expensive and bulky equipment, and the prolonged detection time. Therefore, there is a need for the development of a simple, affordable and responsive substrate for DNA microarray.

SUMMARY

Embodiments described herein are related to a one-step surface modification method with 3-aminopropyl trimethoxysilane (APTMS), which was developed and applied for DNA immobilization on paper via ionic adsorption. X-ray photoelectron spectroscopy (XPS), Infrared spectra (FT-IR), and fluorescence detections were employed to characterize the surface modification and the subsequent DNA immobilization. Incubation conditions of time and temperature were evaluated, and the adsorption mechanism was studied systematically. Furthermore, this one-step DNA immobilization method was successfully used in a paper-based device for the pathogen detection of *Giardia lamblia*. Compared with conventional methods, which use abundant cross-linking reactions, the described method is simpler, faster, and lower-cost, and will provide a simple low-cost method for various biological applications, such as point-of-care diagnosis in resource-poor settings.

Certain embodiments are directed to a probe array comprising an APTMS modified surface and a plurality of probes immobilized on the modified surface. The probes can be nucleic acid probes. In certain aspects the nucleic acid probes are DNA probes.

Other embodiments are directed to methods of making an array comprising: (a) treating a paper surface with 1, 2, 3, 4, 5 to 6, 7, 8, 9, 10% w/v APTMS or equivalent silane in ethanol for 15, 20, 25, 30 to 35, 40, 50, 55, 60 min at 15, 20, 25 to 30° C.; washing the treated paper surface with ethanol and deionized water; and optionally drying the modified, washed paper surface. In certain aspects the paper surface is treated with 5% w/v APTMS. In certain aspects silanes include, but are not limited to (3-Aminopropyl)triethoxysilane; 3-Aminopropyl)trimethoxysilane; m-Aminophenyltrimethoxysilane; p-Aminophenyltrimethoxysilane; p,m-Aminophenyltrimethoxysilane; 4-Aminobutyltriethoxysilane; m, p (Aminoethylaminomethyl)phenethyltrimethoxysilane; N-(2-Aminoethyl)-3-aminopropyltriethoxysilane; N-(2-Aminoethyl)-3-aminopropyltrimethoxysilane, 2-(4-Pyridylethyl)triethoxysilane; N-(6-Aminohexyl)aminopropyltrimethoxysilane; (3-Glycidoxypropyl)trimethoxysilane; (3-Glycidoxypropyl)triethoxysilane; 5,6-Epoxyhexyltriethoxysilane; (3-Mercaptopropyl)trimethoxysilane; (3-Mercaptopropyl)triethoxysilane; 3-Chloropropyltrimethoxysilane; 3-Chloropropyltriethoxysilane; (p-Chloromethyl)phenyltrimethoxysilane; m,p ((Chloromethyl)phenylethyl)trimethoxysilane; (3-aminopropyl)-trimethoxy-silane or APTMS; (3-aminopropyl)-triethoxy-silane or APTES); [3-(2-aminoethyl)aminopropyl]trimethoxy-silane or DATMS or DAMO); (3-Mercaptopropyl)trimethoxysilane or MPTES); 2-(4-Pyridylethyl)triethoxysilane or PETES); (3-Glycidoxypropyl)trimethoxysilane or EPTMS); and 3-Chloropropyltrimethoxysilane or CPTMS). In particular aspects a silane is selected from 3-aminopropyl trimethoxy silane (APrTMS), 3-aminopropyl triethyl silane (APrTES), 3-aminopropyl trimethoxy silane (APTMS), or 3-aminophenyl triethoxy silane (APTES). In a further aspect the paper surface is treated with APTMS for 30 minutes at 25° C. The method can further comprise immobilizing a probe to the surface of the paper surface.

Still further embodiments are directed to the use of an array described herein comprising contacting a sample comprising a target with an array described herein and detecting the presence or absence of a target in the sample by detecting the binding of the target to the array. The target can be a nucleic acid, a protein, a carbohydrate, or other molecules. In certain aspects the target is a nucleic acid, such as a microbial nucleic acid. The microbe can be a bacteria, virus, or fungus. In other aspects the nucleic acid can be a nucleic acid from a eukaryotic cell. In certain aspects the eukaryotic cell can be a cancer cell or an infected cell.

Still further embodiments are directed to an array produced by the process comprising the steps of: (a) obtaining a paper-based device; (b) treating a surface of the paper-based device with 1 to 10% w/v APTMS in ethanol for 15 to 60 min at 15 to 30° C.; (c) washing the treated paper surface with 95% ethanol and deionized water; and (d) optionally drying the modified, washed paper surface. The process can further comprise immobilizing one or more probes to the treated paper surface.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 3. Reaction scheme between FITC and the APTMS-modified paper-based device (3A), fluorescence images after the addition of FITC without (3B) and with APTMS modification (3C).

FIG. 5. Fluorescence intensities of Cy3-labeled DNA immobilized on APTMS-modified paper with different incubation temperatures (A), and with different incubation times (B).

FIG. 7. Images of the paper-based device after patterning (A), and the calibration curve of *Giardia lamblia* detection via DNA hybridization on the aminosilane-derivatized paper-based device for positive controls (square), negative controls (circle), and background (triangle) (B).

DESCRIPTION

Glass slides have been widely employed for DNA immobilization in DNA microarrays. These microarrays face the limitations of complicated fabrication procedures, time-consuming modification, and expensive instruments. Paper-based devices are one of the excellent ASSURED devices which were defined by the World Health Organization as: affordable, sensitive, specific, user-friendly, rapid and robust, equipment free and deliverable to end-users (Zammatteo et al., *Analytical biochemistry* 2000, 280:143-50). The first paper-based device benefited from the invention of paper chromatography by Martin and Synge in 1952 (James and Martin, *Biochem. J.* 1952, 50:679-90). Shortly afterwards, various paper-based assay platforms have been proposed both in scientific research fields and commercial fields, for instance, the world-famous pregnancy test paper to be considered as another milestone. As such, versatile paper-based devices have been developed within the dipstick assays, the lateral flow assays (LFAs) and the microfluidic paper analytical devices (μPADs) (Aragay et al., *Chem. Rev.* 2011, 111:3433-58; Dou et al., *Anal. Chem.* 2014, 86:7978-86; Dou et al., *Biosens. Bioelectron.* 2016, 87:865-73; Sanjay et al., *Analyst* 2015, 140:7062-81), in which the latter has been firstly proposed by the Whitesides group (Martinez et al., *Angew. Chem. Int. Ed.* 2007, 46:1318-20; Martinez et al., *Lab Chip* 2008, 8:2146-50; Martinez et al., *Proc. Natl. Acad. Sci. USA.* 2008, 105: 19606-11; Liu et al., *Lab Chip* 2011, 11:1041-48), and broadly used in multiplex and quantitative analysis due to the successful integration of paper substrate with microfluidic technology.

Nonetheless, most published paper-based devices are focused on the chemical modification of cellulose for covalent biomolecule immobilization via the cross-linking structure. For example, divinyl sulfone (DVS) was used by Yu et al. (*Langmuir* 2006, 22:11245-50) to immobilize small molecules, proteins, and oligonucleotides covalently onto cellulose membranes, which exhibited dose-dependent responses to probes and stability to prolonged storage. Another amine-reactive, homobifunctional linker 1, 4-phenylenediisothiocyanate (PDITC) was employed by Araujo et al., (*Anal. Chem.* 2012, 84:3311-17) to active the amine-functionalized cellulose surface for the covalent attachment of ssDNA, which led to the rapid target hybridization via capillary transport. Although the aforementioned covalent biomolecular immobilization strategies have been successfully employed in biological detections, most of them required multiple modification steps and were suitable only for certain modified DNA probes, which both led to the cost increasing (Yu et al., *Langmuir* 2012, 28:11265-73). Therefore, a simple and versatile technique for oligonucleotides immobilization onto cellulose paper-based device is highly imperative.

Described herein is a simple one-step surface modification method to immobilize DNA probes on paper, avoiding redundant cross-linking reactions used in conventional methods. Particularly, the Cy3-labeled DNA capture probe was simply and efficiently immobilized on the aminosilane-derivatized paper via the ionic interactions between the positive-charged paper surface and negative-charged DNA probes, after one-step surface modification with 3-aminopropyl trimethoxysilane (APTMS). Moreover, comparison experiments were performed within different immobilization substrates (the cellulose paper and glass slides) and immobilization methods (physical adsorption and covalent bonding). In addition, X-ray photoelectron spectroscopy (XPS), fluorescence detections, and FT-IR spectra were employed to characterize the surface modification and the subsequent DNA immobilization. Incubation conditions of time and temperature were optimized, and pH influence on DNA immobilization was studied systematically to verify the above adsorption mechanism. Furthermore, this aminosilane-derivatized paper-based device was successfully applied for the pathogen detection of Giardia lamblia with the limit of detection of 22 nM. To the best of our knowledge, it is the first attempt to conduct a systematical study exploiting the cellulose paper for one-step DNA immobilization to avoid the redundant cross-linking reaction used in conventional methods as illustrated in Scheme 1 (FIG. 1). Compared with those conventional methods, this method is simpler, faster and lower-cost, which provides a significant asset and accessible tool for point-of-care diagnostics, especially in low-resource settings.

As shown in Scheme 2 (FIG. 2), DNA probes were simply immobilized on the aminosilane-derivatized paper-based device via the ionic adsorption, after one-step surface modification with APTMS, avoiding redundant cross-linking reactions. DNA was known to be negative charged due to its backbone phosphate (Fritz et al., Proc. Natl. Acad. Sci. USA. 2002, 99:14142-46). It was proposed that negatively-charged DNA strands were immobilized on the paper surface with the protonated cations (R—$NH_3^+$). XPS, fluorescence tests, and FT-IR spectra were applied to characterize the surface modification and the subsequent DNA probe immobilization. Moreover, the adsorption mechanism was further studied and confirmed through fluorescence performances with different pH values.

Figure 8:
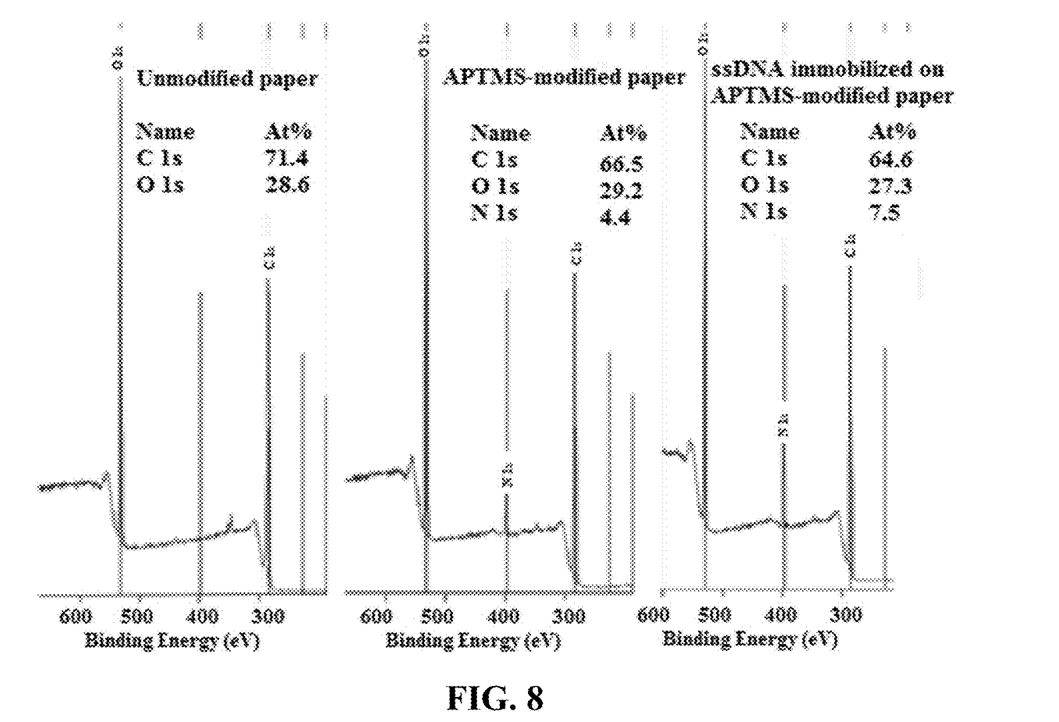
FIG. 8. XPS survey scans of paper devices prior to the aminosilane-derivatization, after the aminosilane-derivatization, and after ssDNA-immobilization on the aminosilane-derivatized paper.

X-ray photoelectron spectroscopy (XPS) surface analysis was performed to verify the surface modification and subsequent DNA functionalization of cellulose papers. Based on XPS elemental compositional results (Table 1, FIG. 8), only carbon ($C_{1s}$ peak at 284 eV) and oxygen ($O_{1s}$ peak at 530 eV) were detected at the surface of unmodified cellulose paper (He et al., Anal. Chem. 2013, 85:1327-31; Malekghasemi et al., Talanta 2016, 159:401-11; Zhang and Lee, Appl. Surf Sci. 2015, 327:233-40). After surface modification with APTMS, the appearance of a nitrogen signal, $N_{1s}$ peak at 399 eV, with atomic percentage estimated to be ~4.4% revealed that certain amount of amino groups was introduced into cellulose paper via the silane coupling technique. Moreover, the XPS analysis of ssDNA-functionalized APTMS-modified paper disclosed the immobilization of ssDNA on the modified paper since the atomic percentage of N increased from 4.4% to 7.5%. The ratio $O_{1s}/C_{1s}$ remained similar, which was found to be 40.1%, 44.0%, and 42.3%, respectively, for the above samples. Moreover, the ratio $N_{1s}/C_{1s}$ was found to increase from 6.6% to 11.6%, which explicitly indicated the immobilization of ssDNA onto APTMS-modified paper-based device.

TABLE 1

XPS compositional analysis of paper devices prior to aminosilane-derivatization, after aminosilane-derivatization, and after ssDNA-immobilization on aminosilane-derivatized paper

| XPS analysis, atomic percentage | Unmodified paper | APTMS-modified paper | ssDNA-functionalized APTMS-modified paper |
|---|---|---|---|
| C 1s | 71.4% | 66.5% | 64.6% |
| O 1s | 28.6% | 29.2% | 27.3% |
| N 1s | 0 | 4.4% | 7.5% |

Figure 3A:
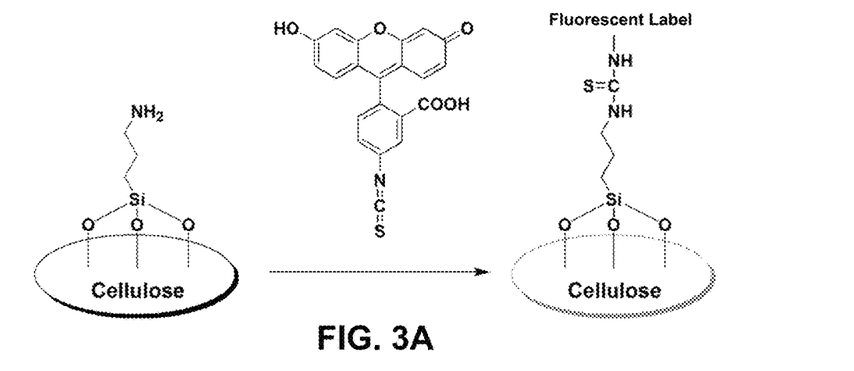
Figure 3B:
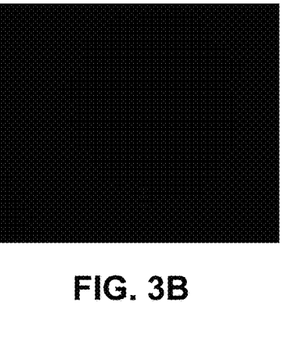
Figure 3C:
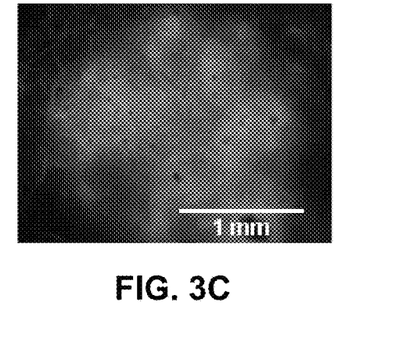

The surface modification of paper device with APTMS was further characterized by exploiting the reaction between the amine-terminated surface and Fluorescein isothiocyanate (FITC), and the reaction mechanism was illustrated in FIG. 3A. The fluorophores were introduced on the paper surface through chemical reactions between isothiocyanate groups and amine groups (Guan et al., Bioresources 2015, 10:1587-98). As can be seen in FIGS. 3B and 3C, the clear fluorescence emitted on the APTMS-modified paper-based device, while non-fluorescence emitted on the unmodified paper-based device. FITC on unmodified paper was carried away by the washing buffer and thus non-fluorescence emitted in this control experiment as shown in FIG. 3B. However, with APTMS surface modification, the active amine groups were introduced and reacted with FITC covalently, and strong green fluorescence signals were captured in the detection zone (FIG. 3C). Moreover, the fluorescence intensity increased by ~30 folds from 246 to 7,493, which indicated the high efficiency of the surface modification on cellulose papers with APTMS. Fluorescence characterization confirms the reliable modification with amine groups on the paper surface.

Figure 9:
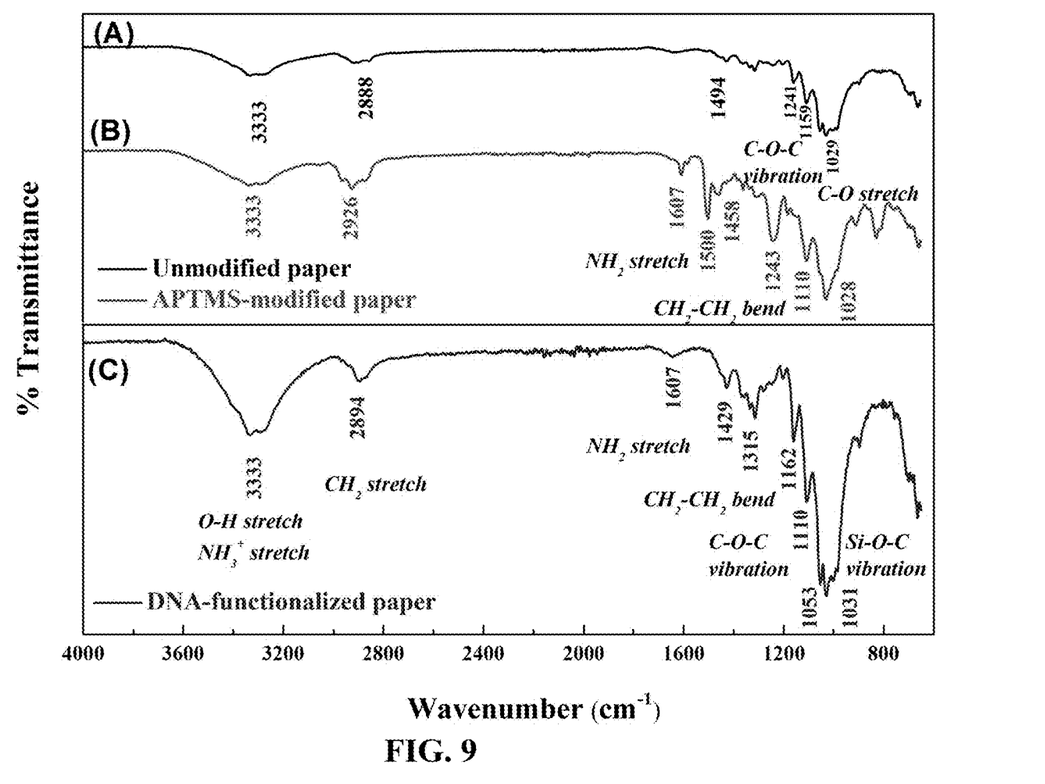
FIG. 9. IR spectra of IR spectra of native paper (A), APTMS-modified paper (B), and DNA-functionalized APTMS-modified paper (C).

The FT-IR spectra of the unmodified paper, the APTMS-modified paper, and the DNA-functionalized aminosilane-derivatized paper were recorded by using Spectrum 100 FT-IR Spectrometer, Perkin Elmer. The FT-IR spectra in FIG. 9A showed typical peaks of cellulose paper: O—H stretching vibration region from ca. 3200 to 3500 $cm^{-1}$, C—O—C asymmetric vibration from ca. 1162 to 1125 $cm^{-1}$, and C—O stretching vibration region from ca. 1030 to 1060 $cm^{-1}$ (Koga et al., J. Mater. Chem. 2011, 21:9356-61; Kao and Hsu, Microfluid Nanofluid 2014, 16:811-18; Zhao et al., Biosens. Bioelectron. 2016, 79:581-88). In the case of the APTMS-modified paper, as shown in FIG. 9B, the absorption peaks around ca. 1029 $cm^{-1}$, ca. 1607 $cm^{-1}$, and ca. 2920 $cm^{-1}$ were ascribed to the Si—O—C bond, $NH_2$ bending and $CH_2$ stretching vibration, respectively, which indicated the existence of aminopropyl silane groups (Kao and Hsu, Microfluid Nanofluid 2014, 16:811-18). In addition, the bending vibration of methylene groups was observed in the region from ca. 1460 to 1500 $cm^{-1}$. As to the DNA-functionalized APTMS-modified paper shown in FIG. 9C, the absorption bands of —$NH_3^+$ and —OH stretching vibration appeared from ca. 3280 to 3380 $cm^{-1}$, while the $NH_2$ bending vibration at ca. 1607 $cm^{-1}$ became weaker, which could be assigned to the transformation from —$NH_2$ to —$NH_3^+$. Moreover, as shown in FIG. 9C, vibration peaks from ca. 1100 to 1500 $cm^{-1}$, which were illustrated to C—O bonds and methylene bending vibrations (Zhao et al, Biosens. Bioelectron. 2016, 79:581-88), became obviously much weaker in comparison of those in the APTMS-modified paper. This phenomenon may be due to the electrostatic interaction between the positive-charged paper surface and negative-charged DNA molecules, which weakened the above vibrations (Li et al., *J. Am. Chem. Soc.* 2002, 124: 9639-47).

Figure 1A:
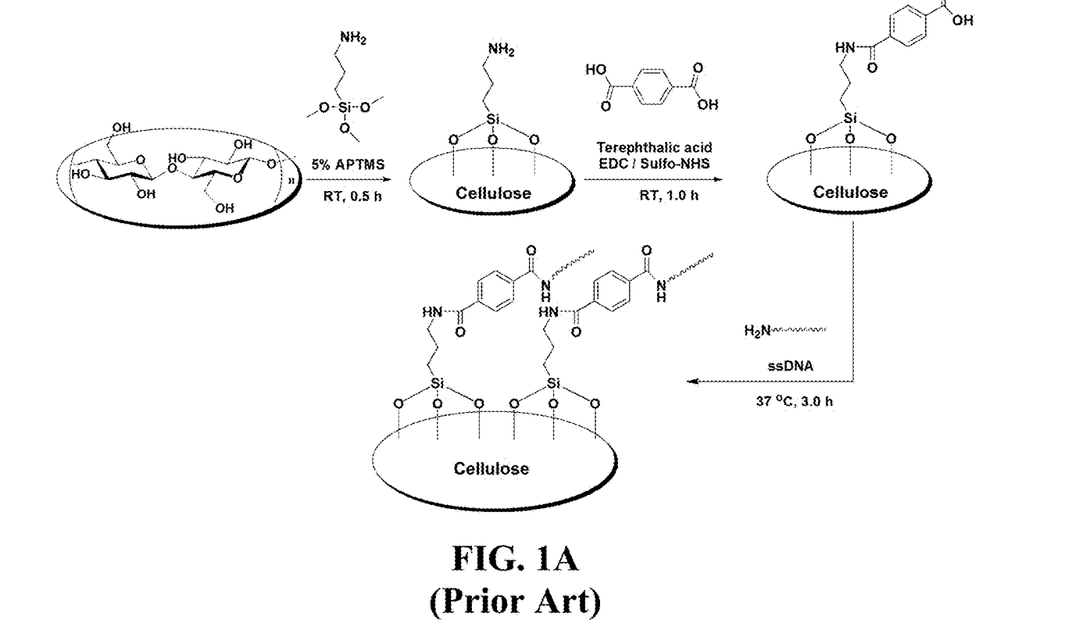
FIGS. 1A-1B. Scheme 1. ssDNA immobilization onto aminosilane-derivatized paper covalently via terephthalic acid cross-linking reaction (1A), or onto glass slides via terephthalic acid cross-linking reaction (1B).
Figure 1B:
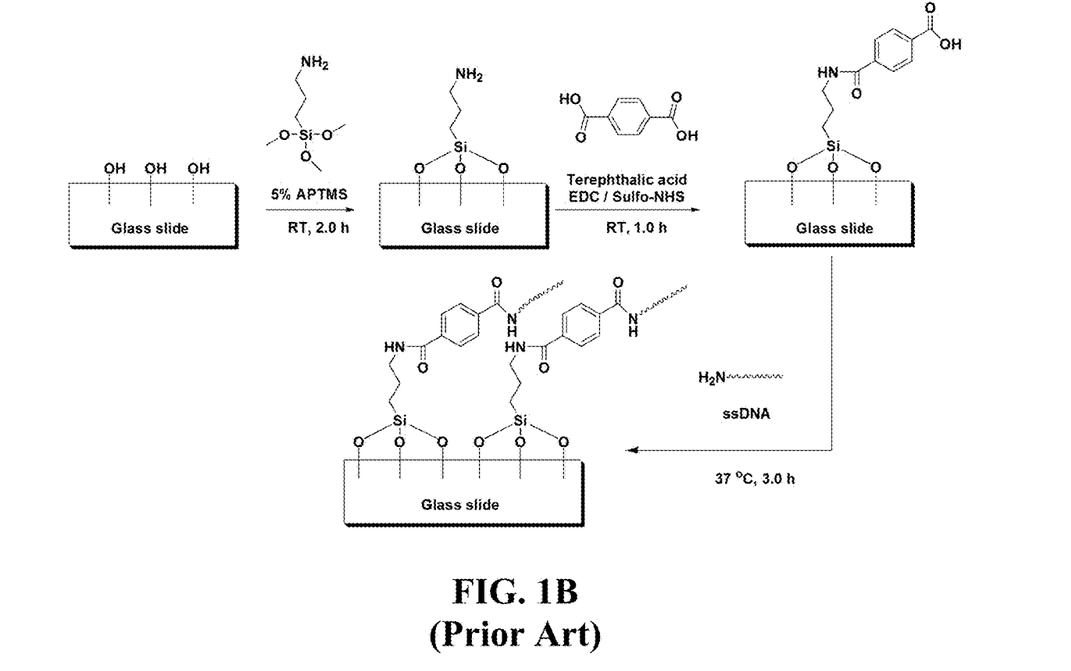
Figure 4A:
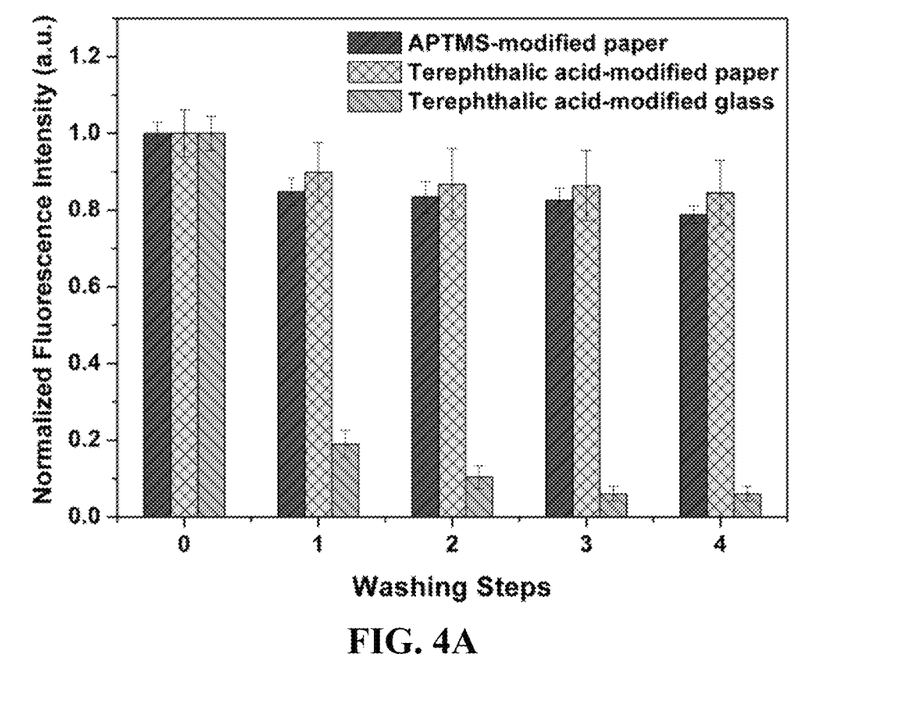
FIGS. 4A-4B. (4A) The normalized fluorescence intensities of Cy3-labeled ssDNA after being subjected to several washing steps (exposure time, 9 ms). Cy3-labeled ssDNA was either ionically adsorbed onto APTMS-modified paper, covalently immobilized onto paper via terephthalic acid (TA), or covalently immobilized onto glass slides via terephthalic acid. (4B) Fluorescence images of Cy3-labeled ssDNA adsorbed onto aminosilane-derivatized paper before washing and after three washing steps (a), compared to covalent ssDNA immobilization on paper via terephthalic acid cross-linker before and after three washing steps (b), and covalent ssDNA immobilization on glass slides via terephthalic acid cross-linker before and after three washing steps (c).
Figure 4B:
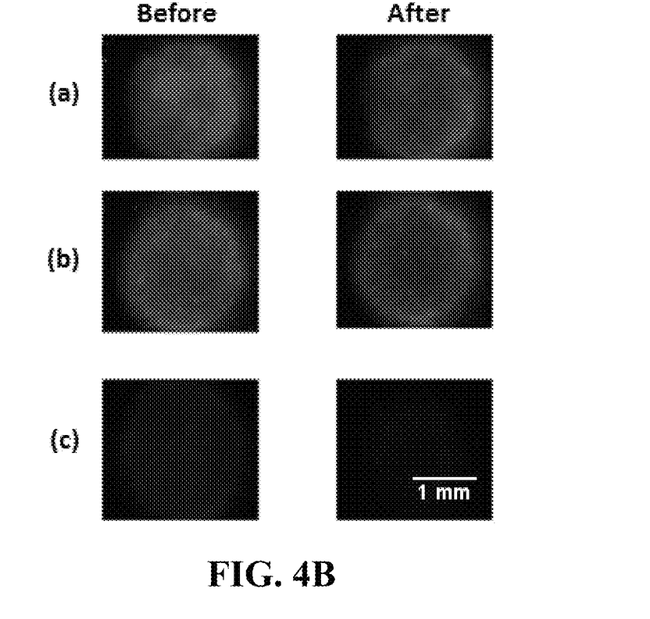

Fluorescence detection of the ssDNA-functionalized APTMS-modified paper-based device was carried out on the Fluorescence Microscopy. To confirm the performance of the novel probe immobilization method on the paper substrate, Cy3-labeled ssDNA was immobilized via the direct adsorption onto the APTMS-modified paper, while a control paper-based device was fabricated in which ssDNA was covalently immobilized on the APTMS-modified paper via the cross-linking reaction with terephthalic acid (TA), as shown in Scheme 1 (A) (FIG. 1). Astonishingly, the results turned out that the paper-based device for one-step adsorption of ssDNA onto the APTMS-modified paper exhibited the comparative immobilization level (80%) to its covalently immobilized counterpart (84%) after several washing steps as shown in FIG. 4. On the other side, normalized fluorescence intensities on TA-modified glass slides (as shown in Scheme 1 (B) (FIG. 3)) decreased to 6.0%, which became much lower than those on the above substrates during the washing steps. These results were mainly due to the insufficient absorbability, since some Cy3-labeled ssDNA probes were washed away on TA-modified glass slides while increasing washing steps. The corresponding fluorescence images in FIG. 5 were displayed before washing steps and after the third washing on different substrates, which agreed well with the normalized fluorescence intensities analysis. The above results clearly indicated that the APTMS-modified paper-based device allowed for sufficient DNA immobilization, and could be used as a reliable surface-modified device avoiding any cross-linking reactions.

Figure 5A:
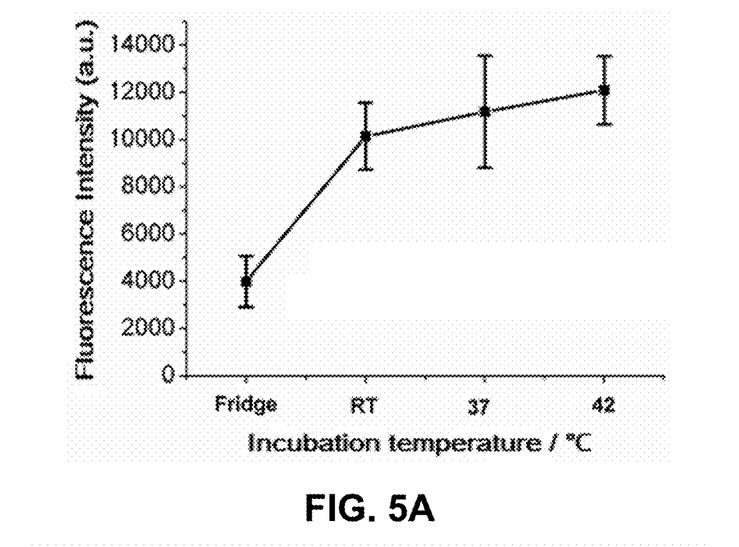
Figure 5B:
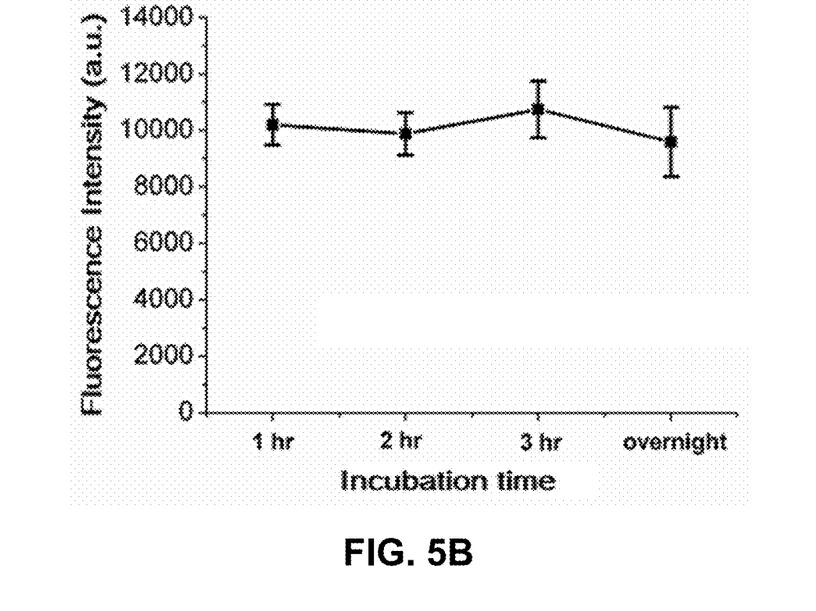

To apply this immobilization method in biological applications, condition optimization was studied. The incubation temperature, as an important factor during DNA detection, would affect the physical adsorption as well as fluorescent signals. Incubation assays at different typical temperatures, 4° C. (in the fridge), 25° C. (room temperature), 37° C., and 42° C. were investigated for 3.0 h and the results are shown in FIG. 5A. The incubation at 42° C. gave a higher fluorescence signals comparing with others. Hence, 42° C. was used in the following DNA detection. Moreover, the incubation time would also affect the immobilization efficiency on the paper-based device. In addition, a series of incubation times of 1 h, 2 h, 3 h and overnight (~12 h) were studied in the context. Interestingly, it was found that fluorescence signals changed slightly within above incubation times as shown in FIG. 5B. Therefore, 1 hour of incubation time was sufficient and selected in the subsequent experiments.

Figure 6:
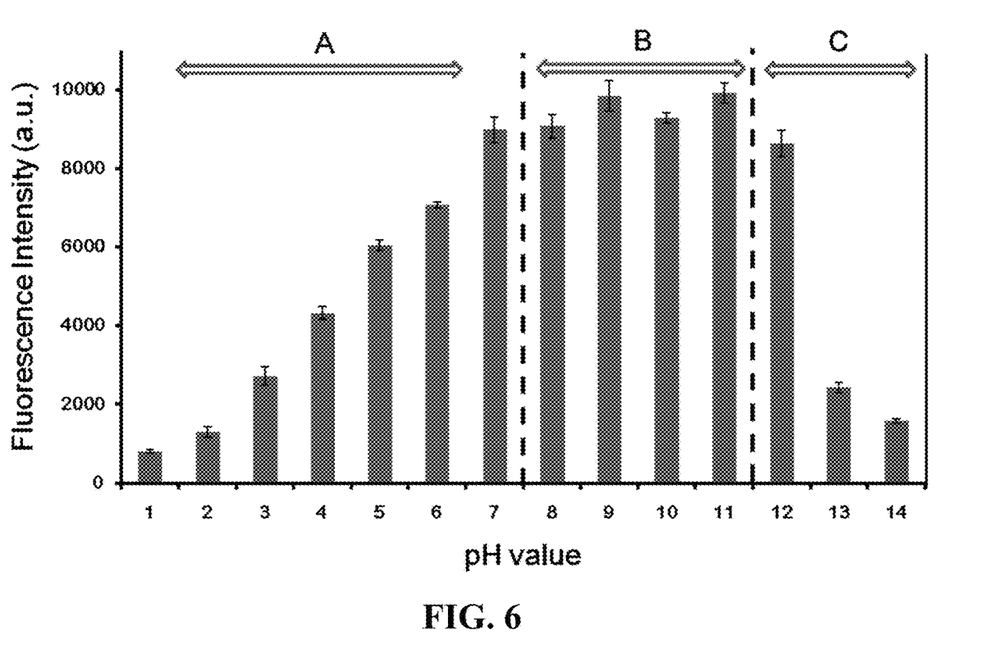
FIG. 6. Fluorescence intensities of Cy3-labeled DNA on APTMS-modified paper-based device vs. different pH from 1.0 to 14.0. (n=6).

The mechanism of DNA immobilization was further investigated as following. Cy3-labeled DNA was prepared and then pipetted on the APTMS-modified paper-based device with different pH values from pH 1.0 to 14.0, respectively. The fluorescence intensities were obtained via the Fluorescence Microscopy, and the results were shown in FIG. 6. The variation tendencies of fluorescence intensities with different pH values could be divided into three regions (A, B, and C). In detail, the fluorescence intensities in region A increased steadily from pH 1.0 to pH 7.0, and maintained as a plateau in region B from pH 7.0 to 12.0, and then decreased distinctly in region C when pH above 12.0. As reported previously, the three $pK_a$ values of phosphoric acid were 2.1, 7.2, 12.5, respectively (Christ et al., *Chemistry* 2011, 17:8524-28; Demirel, *Chemphyschem.* 2014, 15:1693-99; Wang and Bard, *Anal. Chem.* 2001, 73:2207-12), and the $pK_a$ of APTMS-$NH_3^+$ was found to be 10.6 (Niu et al., *Chem. Commun.* 2008, 4463-65; Shalev et al., *Sensors* (Basel) 2009, 9:4366-79). Therefore, the amount of negative-charged ions ($PO_4^{3-}$) in DNA structures increased gradually as pH increasing, resulting in the favorable tendency of DNA immobilization via the ionic adsorption as shown in region A. In contrast, the protonated cations (R—$NH_3^+$) were dominated on the surface in lower pH and less negatively-charged DNA probes were immobilized on the paper as pH increases. Hence, in region B, the fluorescence intensities remained similar with no significant difference, mainly due to the competitive effects from $PO_4^{3-}$ in DNA structures and R—$NH_3^+$ on the paper surface. Moreover, R—$NH_2$ molecules were dominated when pH was above 11.0 in region C, and impeded the positively-charged surface modification of paper-based devices, leading to the insufficient DNA immobilization, which agreed well with the lower fluorescence intensities observed. These results verified our previous proposal that DNA probes were immobilized on the APTMS-modified paper-based device via the ionic adsorption.

Figure 7A:
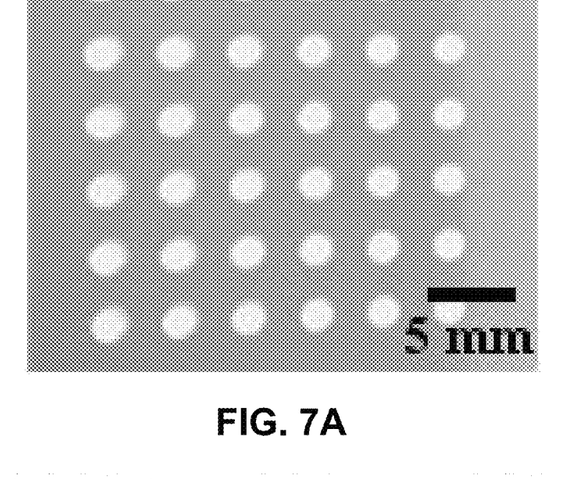
Figure 7B:
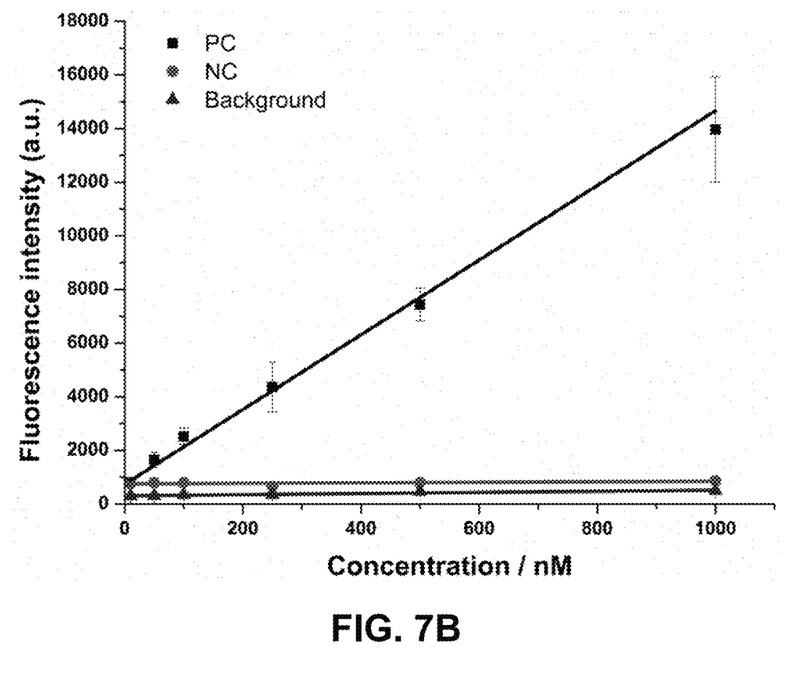

A diagnostic application was developed using the methods described herein. Briefly, DNA capture probes were firstly immobilized onto the APTMS-modified paper-based device via the simple, one-step probe grafting on paper, and followed by DNA hybridization with the target pathogen. *Giardia lamblia* was used as a model pathogen in this work to test the effectiveness of this device in FIG. 7A. As such, *Giardia lamblia* Amplicon was employed as the positive control (PC), with *N. Meningitis* Amplicon as the negative control (NC), and PBS buffer as the background. Fluorescent signals were collected within each detection zone. As the *Giardia lamnblia* DNA concentration increased in the range from 10 to 1000 nM, as shown in FIG. 7B, the fluorescence intensity was proportional to the sample concentration, with a correlation coefficient of 0.98. There was no significant change in fluorescence intensities while increasing the concentration of negative control samples and PBS buffer. The limit of detection of Cy3-*Giardia lamblia* DNA was determined as low as 22 nM, which is comparable to, or even lower than those on glass slides reported by other researchers (Schlapak et al., *Langmuir* 2006, 22:277-85; Pirriet al., *Anal. Chem.* 2004, 76:1352-58; Le Berre et al., *Nucleic Acids Res.* 2003, 31:88-95).

A one-step surface modification method has been developed for simple DNA immobilization on the paper-based device. X-ray photoelectron spectroscopy (XPS), fluorescence characterization, and FT-IR spectra were used to confirm the surface modification and the subsequent DNA immobilization. Incubation conditions of time and temperature were optimized for certain application and were found to be 1 h and 42° C., respectively. The pH influence on DNA immobilization was studied systematically to further verify the mechanism of DNA immobilization (the ionic adsorption) on the APTMS-modified paper-based device. This device was successfully applied for the detection of *Giardia lamblia* DNA with the LOD as low as 22 nM. This simple one-step surface modification and novel DNA immobilization method on the low-cost paper-based device has great potential for point-of-care diagnosis and will broaden the application of paper-based bioassays in resource-poor settings.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Fabrication of Paper-Based Device.

Whatman No. 1 chromatography paper was used via a modified protocol to fabricate the epoxy-based negative photoresist (SU-8) detection zone (Martinez et al., *Angew. Chem. Int. Ed.* 2007, 46:1318-20; Martinez et al., *Lab Chip* 2008, 8:2146-50; Martinez et al., *Proc. Natl. Acad. Sci. USA.* 2008, 105:19606-11; Liu et al., *Lab Chip* 2011, 11:1041-48). Briefly, the chip pattern was designed using Illustrator software and printed on a transparency as the photomask. Then the paper-based device was created from the SU-8 coated wafer with the photomask under a UV exposure system for 20 s. The unpolymerized photoresist was removed by acetone and 70% isopropyl alcohol, and the patterned paper was allowed to air dry at ambient temperature for 20 min. The diameter of each detection zone is 2.0 mm.

Surface Modification of Cellulose Paper.

The patterned paper device was placed on an orbital shaker after plasma treatment for 4 min and then treated with 5% APTMS in ethanol for 30 min at room temperature. The patterned paper was washed three times with 95% ethanol and deionized water, respectively, to remove excess reagents, and then dried. The aminosilane-derivatized paper-based device was stored in dark at 4° C. before probe immobilizing.

DNA Probe Immobilization on the Aminosilane-Derivatized Paper Via Ionic Adsorption and Covalent Cross-Linking Reaction.

Figure 2:
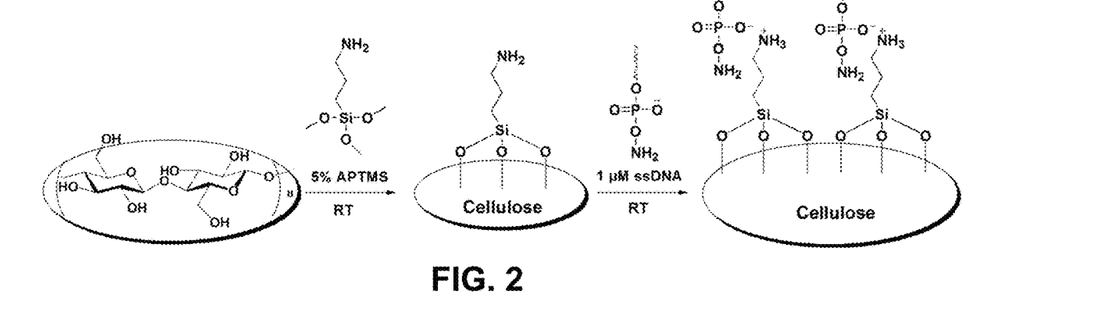
FIG. 2. Scheme 2. ssDNA immobilization onto aminosilane-derivatized paper via a direct one-step APTMS method.

Cy3-labeled ssDNA was used in both methods (Wang and Li, *J. Agric. Food Chem.* 2007, 55:10509-16; Dou et al., *Talanta* 2015, 145:43-54; Sanjay et al., *Sci Rep-Uk* 2016, 6:30474-83). Briefly, 2 μL 1 μM Cy3-labeled ssDNA was added on each detection zone and then immobilized onto aminosilane-derivatized cellulose substrate through ionic interactions between positively charged amino groups on APTMS and the negatively charged phosphate backbone of DNA as shown in FIG. 2.

Moreover, terephthalic acid in a 1:1 mixture solution of 1-ethyl-3[dimethylaminopropyl] carbodiimide hydrochloride (EDC, 0.4 M) and N-Hydroxysuccinimide (NHS, 0.1 M) was added on each detection zone of the above APTMS-modified paper, and followed by the incubation for 1 h at room temperature. 2 μL 1 μM Cy3-labeled ssDNA was added and incubated on each detection zone at 37° C. for 3 h. The DNA probes were thus immobilized onto the terephthalic acid-modified paper via the covalent cross-linking reaction. Scheme 1(A)(FIG. 1) shows that aminated DNA probes reacted indirectly with epoxide silane modified cellulose fibers through the use of a cross-linker, terephthalic acid.

DNA Probe Immobilization on the Aminosilane-Derivatized Glass Slides Via Covalent Cross-Linking Reaction.

The conventional modification and functionalization of glass slides via the covalent cross-linking reaction were conducted using an established procedure. Briefly, glass slides were cleaned with 10% NaOH solution for 10 min at ~100° C., and followed by a piranha solution (70:30 v/v, sulfuric acid to 30% hydrogen peroxide) for 1 h at ~80° C. The glass slides were rinsed with water and dried prior to use. The cleaned glass slides were then treated with 5% APTMS in ethanol for 2 h at room temperature, and washed three times with 95% ethanol and deionized water, respectively. Then the glass slides were immersed in the 10% w/v terephthalic acid solution with a 1:1 mixture solution of 1-ethyl-3[dimethylaminopropyl] carbodiimide hydrochloride (EDC, 0.4 M) and N-Hydroxysuccinimide (NHS, 0.1 M), and followed by the incubation for 1 h at room temperature. After being washed with acetone and deionized water and dried, a polydimethylsiloxane (PDMS) plate was assembled with the terephthalic acid-modified glass slides to form sample reservoirs with the diameter of 2.0 mm. Then 2 μL 1 μM Cy3-labeled ssDNA was added and incubated on each reservoir at 37° C. for 3 h. The DNA probes were thus immobilized onto the terephthalic acid-modified glass slides via the covalent cross-linking reaction. Scheme 1(B)(FIG. 1)(Park et al., *Bioconjug. Chem.* 2010, 21:1246-53).

The invention claimed is:

1. A probe array comprising a one-step APTMS modified paper surface and a plurality of nucleic acid probes immobilized on the modified paper surface via ionic adsorption.

2. The probe array of claim 1, wherein the plurality of nucleic acid probes are DNA probes.

3. A method for preparing a paper surface for one-step immobilization of a DNA probe via ionic adsorption, the method comprising:
    treating the paper surface with 1 to 10% w/v silane in ethanol for 15 to 60 min at 15 to 30° C.;
    washing the treated paper surface with 95% ethanol and deionized water;
    drying the modified, washed paper surface.

4. The method of claim 3, wherein the silane is APTMS.

5. The method of claim 3, wherein the paper surface is treated with 5% w/v silane.

6. The method of claim 3, wherein the paper surface is treated with silane for 30 minutes at 25° C.

7. The method of claim 3, further comprising immobilizing a DNA probe to the surface of the paper surface.

8. A method for detecting the presence or absence of a target in a sample comprising:
    contacting the sample comprising the target with the array of claim 1; and
    detecting the presence or absence of a target in the sample by detecting the binding of the target to the array.

9. The method of claim 8, wherein the target is a nucleic acid.

10. The method of claim 9, wherein the nucleic acid is microbial nucleic acid.

11. The method of claim 10, wherein the microbe is a bacteria, virus, or fungus.

12. An array produced by the process comprising the steps of:
    (a) obtaining a paper-based device;
    (b) treating a surface of the paper-based device with 1 to 10% w/v silane in ethanol for 15 to 60 min at 15 to 30° C.;
    (c) washing the treated paper-based device surface with 95% ethanol and deionized water;
    (d) drying the modified, washed paper-based device surface; and
    (e) treating the paper-based device surface with a plurality of nucleic acid probes, wherein the plurality of nucleic acid probes are immobilized on the paper-based device surface via ionic adsorption to form an array.

13. The array of claim 12, wherein the silane is APTMS.

* * * * *